United States Patent [19]
Curbelo

[11] 3,976,862
[45] Aug. 24, 1976

[54] FLOW STREAM PROCESSOR

[75] Inventor: Raul Curbelo, Lexington, Mass.

[73] Assignee: Block Engineering, Inc., Cambridge, Mass.

[22] Filed: Mar. 18, 1975

[21] Appl. No.: 559,482

[52] U.S. Cl. ........................ 235/151.34; 235/150.3; 356/39
[51] Int. Cl.² ................. G06F 15/20; G01N 33/16; G06F 15/42
[58] Field of Search .................. 235/150.3, 151.34; 250/373, 365; 356/39

[56] References Cited
UNITED STATES PATENTS

| 3,600,563 | 8/1971 | Forter et al. ................ 235/150.3 |
| 3,822,095 | 7/1974 | Hirschfeld ...................... 356/39 |

*Primary Examiner*—Edward J. Wise
*Attorney, Agent, or Firm*—Schiller & Pandiscio

[57] ABSTRACT

A flow stream processor particularly adapted for use in blood cell processing, and having discriminator circuits for selecting a particular group of cells from a large population, thereby permitting digital processing of data relative to the cells to be carried on only with respect to the particular group. Additionally the system includes circuitry for automatically adjusting flow stream velocity in accordance with an error signal developed proportionally to the phase difference between signals received from the first and last detectors along the flow stream resulting from transmit of the same cell.

15 Claims, 1 Drawing Figure

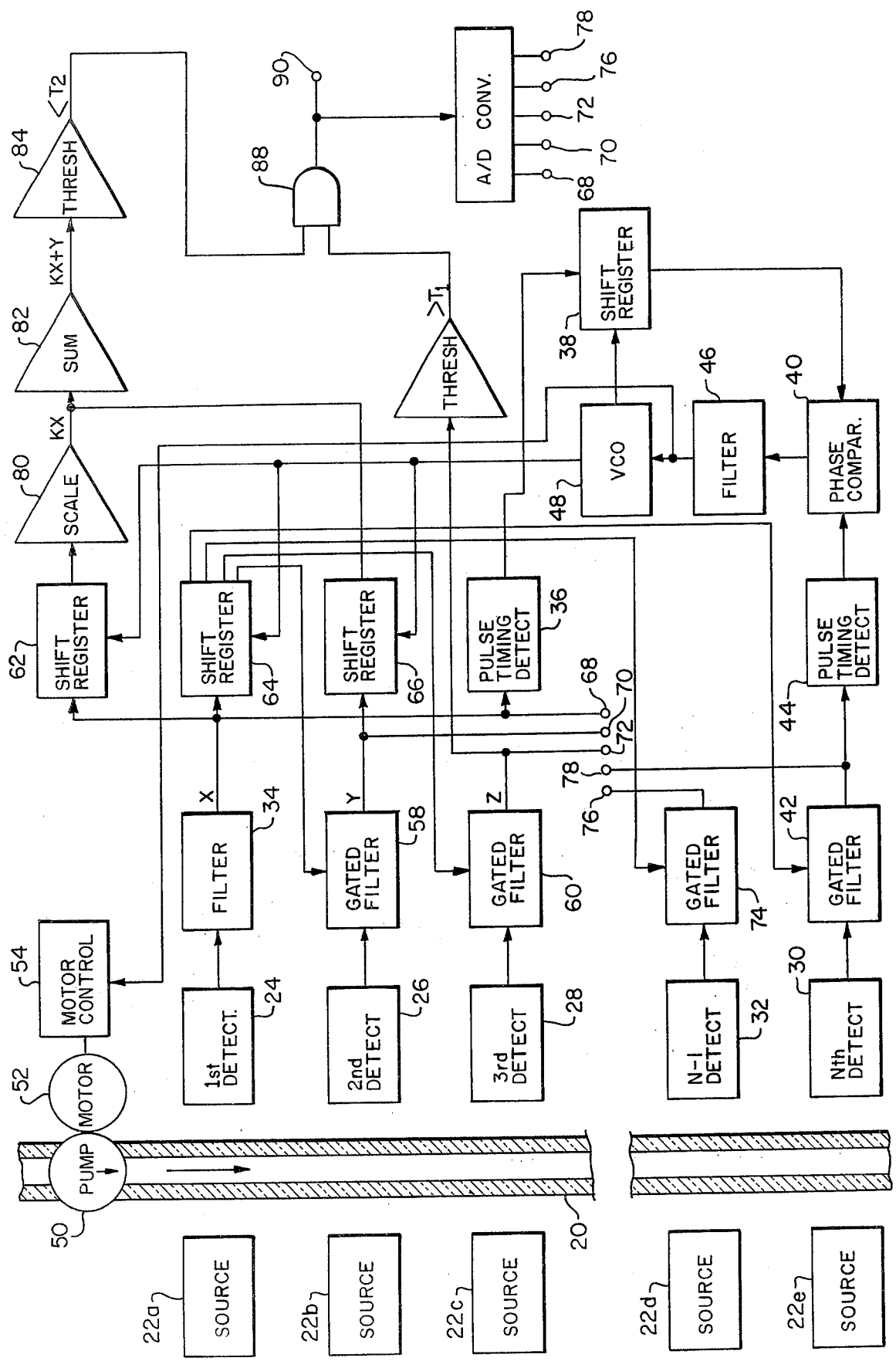

FLOW STREAM PROCESSOR

This invention relates to processing of large populations of particles in flow stream, and more particularly to processing groups or classes of histological specimens.

Frequently, one may wish to perform some process, such as taking of a measurement or the like, on only one class of items in a large population. For example, if one wishes to make a differential white cell count in blood, the white cells constitute a very small class in comparison to the total blood cell populations. Typically, the ratio of red to white cells is about a thousand or more to one. If all of the cells are suspended in a fluid in a flow stream so that all of the cells in the population can be passed sequentially by a measuring or examing station, an inordinately long time is required to obtain a statistically valid sample of the white cells and a great deal of effort is wasted in differentiating the undesired red blood cells from the white cell class.

The prior art has typically turned to a number of separation techniques to preprocess blood so that the group of white cells is preliminarily differentiated from the red blood cells. For example, the red cells can be removed by hemolysis, which unfortunately can also damage or destroy a number of the fragile white blood cells. Histological specimens are sometimes presorted by centrifugation, but this technique is not really selective, can be extremely damaging to the cells and does not prepare suitable specimens for many purposes.

The present invention is therefore primarily directed to apparatus for and a method of preprocessing populations of items in a flow stream so that information regarding selected subpopulations or classes can be readily obtained in a comparatively brief period of time.

To this end, the present invention employs a gating system using a simple set of discriminating characteristics so that the items can be moved through the flow stream at extremely high speed and data relevant only to one or more selected groups of items need be fully processed.

Generally, the present invention is an improvement over known equipment in which means, such as a capillary tube, are provided for confining the population of items, such as blood cells, to a flow stream in which the cells move seriatim, i.e., in single file, one or more detection means being positioned in sequence along said flow stream. A plurality of signal sources are similarly positioned along the flow stream, each opposite a corresponding one of the detectors. Thus for example, a single blood cell can be passed in sequence by the several detectors, modulating the signal from each source. As is well known in the art, the several signal sources each typically provides a different type of signals, one or more of which are modulated by a particular cell in a manner characteristic of that type of cell. The data provided by the several output signals from the detectors then can be combined to provide a description characteristic of that type of cell. For example, one can assume that one of the detectors sees light from a corresponding signal source, scattered at a particular angle; a second detector will respond only to light of a particular wavelength transmitted by a cell; a third detector for example will respond only to light of a particular wavelength reflected from the cell, etc. It is known that a combination of a number of cell characteristics, e.g., absorption, reflection, scattering, pulse width, capacitance, etc., provide a set of parameters which can accurately indentify each cell type. However, if one seeks to measure a particular group which forms a very small part of a large population, a tremendous amount of time and effort may be wasted if every cell is to be minutely examined for every parameter by all the detectors and all the resulting data are stored and processed for all the cells. Typically, such storage and processing is done in digital form in a general purpose computer and requires that the signals from the individual detectors be converted to digital form by the usual known analog-digital converters.

The present invention essentially preprocesses signals from the detectors so that only signals from a desired group of cells are converted to digital form for processing, the remaining cells (usually a very large majority) being either simply counted or ignored thereby substantially reducing the memory and computation capabilities of an associated computer, as well as substantially reducing the amount of storage and/or computation time required to cull out only the information pertinent to the selected class or group of items in the total population.

It will also be appreciated that notwithstanding the preprocessing thus generally described with regard to the present invention, the total amount of time required to obtain information regarding the selected class of items in additionally limited by the detection process itself, i.e., the time required to obtain each signal from each detector and to time-correlate the several signals so that the latter can each be unequivocally attributed to the same cell. For example, one can correlate the outputs of the several detectors by known sampling techniques wherein the signals from the detectors are time gated, i.e., the several detectors will each be sequentially enabled and disabled for predetermined periods of time (i.e., time "windows" are provided). Thus, only those signals which occur during the period of the selected time windows are considered significant or important. Of course, the interval between the time windows is determined by the distances between detectors (usually fixed values) along the flow stream, and by the flow stream speed. Because the latter is subject to perturbations, the time windows must be wide enough so that when correlated they will still overlap notwithstanding flow stream speed variations within a predetermined range. Of course, the wider the time windows, the larger must be the distance between particles or cells or the slower must be the particle velocity, in order to avoid occurrence of multiple signals during a time window.

The present invention permits one to use time windows of much smaller width by virtue of apparatus for providing precise control of flow stream speed, thereby reducing the range of expected flow perturbation.

This control apparatus generally comprises signal delay means, the delay period of which is variable in accordance with a timing signal. The input of the delay means is coupled to the output of the first or upstream detector in the detector sequence, the output of the delay means being in turn connected as one input to a phase detector or comparator. The output of the last or downstream detector in the sequence is connected as another input to the phase detector. The phase detector as usual is intended to provide an output control signal proportional to the phase difference between its two inputs, which preferably have been shaped, etc., so that they are phase-comparable signals. Means are provided for generating the requisite timing signal in accordance with the control signal provided by the output of the phase detector. The timing signal of course is applied to control the delay period of the delay means. It will be apparent that as described this is somewhat similar to a phase-locked system, but here the control or error signal produced by the phase detector is employed to control a delay period. If the delay period initially set in the delay means is approximately equal to the transit time of a particle, cell or other item along the flow stream from the first to the last detector in the sequence, then the timing signal provided by the system described, will vary precisely in accordance with changes in flow velocity, with a duty cycle equal approximately to the delay period. This timing signal preferably is employed to control the timing of the correlation of a selected number of the several detector signal to each other, and also of course is used as a control signal to control the pumping rate at which the cells are passed through the detector sequence.

Other objects of the invention will in part be obvious and will in part appear hereinafter. The invention accordingly comprises the apparatus possessing the construction, combination of elements and arrangement of parts which are exemplified in the following detailed disclosure, and the scope of the application of which will be indicated in the claims. For a fuller understanding of the nature and objects of the present invention, reference should be had to the following detailed description taken in connection with the accompanying drawing wherein there is shown, partly in fragmentary cross-section and partly in block diagram, a system embodying the principles of the present invention.

Referring now to the drawing there will be seen means, in the form of glass capillary 20, for confining a flow stream in which items of a particular population are thereby restricted to a seriatim flow. For example, the inside diameter of the capillary can be limited, in known manner, to a width such that a population of cells, such as blood cells, suspended in a fluid medium, can only flow in single file. Of course, a blood sample, as known to those skilled in the art, is usually diluted, typically with physiological saline solution so that the concentration in terms of the number of blood cells per milliliter is low enough to be sure that the cells when passing through the capillary are reasonably well separated on the average. A number of devices using flow streams of cells in single file are known and have been described, such as in U.S. Pat. No. 3,699,336 to Ehrlich et al., and a host of other patents. Disposed in a sequence along capillary 20 are a plurality of signal sources, 22a, 22b, 22c, 22d and 22e, only five being shown for exemplary purposes. Signal sources 22a and the like can be sources of visible light limited to specific wavelength bands as by appropriate filtering, sources of ultraviolet light or infrared light, sources of fields such as static electrical fields and magnetic fields, and the like. Disposed on the other side of capillary 20 are a plurality of detectors in sequence, first detector 24 being positioned at the upstream end of capillary 20 and being disposed with respect to source 22a so that the passage of an item of interest, such as a cell, through capillary 20 between source 22a and detector 24 will modulate the signal from source 22a. When the modulated signal is detected by detector 24, the latter will produce a corresponding signal. For example, assume source 22a is a source of light of a particular limited wavelength band and detector 24 is sensitive to light to that wavelength band. Passage between source 22a and detector 24 of a cell stained so that at least a part of the light from source 22a is absorbed, will cause detector 24 to produce an electrical output in the form of a pulse, the width of which is approximately equal to the transit time of the cell past the detector. Similarly, the system of the invention is provided with a second detector 26 which is intended to detect modulation of the signal provided by source 22b, and a third detector 28 which is positioned and arranged to detect modulation of the signal from source 22c. As noted, the system is also provided with an Nth or last detector 30 which is positioned downstream opposite source 22e for detecting modulated signals from the latter, and N−1 detector 32 which is positioned with respect to source 22d for detecting modulated signals from the source also. It will be apparent to those skilled in the art that a separate source may be, in some instances, not necessary is the cell or particle in the flow stream in capillary 20 itself serves as a source, for example by being radioactive or the like. As thus described, the system including a capillary, a plurality or sequence of signal sources and a like sequence of corresponding detectors is known in the art.

The present invention however includes a servo system which permits the establishment of optimally small sampling intervals for each of the signals produced by the detectors, controls the flow velocity of the stream within capillary 20, and lastly permits continuous correlation automatically of all of the various detector signals. To this end, the output of first detector 24 is coupled to the input of filter circuit 34. The latter may also include any of a number of known circuits which shape an output pulse to have a width proportional to the input pulse from detector 24, but typically with a wave envelope of fixed shape such as a triangular wave, square wave or the like. The filter insures that the pulse will be devoid of undesirable transients or other perturbations that may be present in the output of detector 24. Filter 34 thus typically may include known filter circuits, analog integrator circuits and the like. The output of filter 34 is connected to the input of pulse timing detector 36. The latter can be any of a large number of known circuits which provide an output pulse having a precise time marker, such as an abrupt leading edge or trailing edge, precisely correlated in time with some aspect of the output of filter 34. For example, if the output of filter 34 is a square wave, the output of pulse timing detector 36 may provide a pulse in which the leading edge is exactly coincident with either the leading or trailing edge, as may be chosen by the designer, of the pulse from filter 34. In the preferred embodiment, pulse timing detector 36 provides an output pulse, the leading edge of which is precisely coincident with the exact center of the pulse provided by filter 34. Typically, if the pulse provided by filter 34 has a triangular wave envelope, then pulse timing detector 36 may simply be a peak detector circuit of known structure.

The output of pulse timing detector 36 is connected to the input of signal delay means, such as shift register 38, which is adapted to transfer a pulse between an input and an output in a time period variable in response to a timing signal. Of course, it is known that shift registers will move a signal from their input to output in accordance with a clocking input, hence, the latter in such case constitutes the requisite timing signal. The output of shift register 38 is connected to one input of phase detection circuit 40. It will be seen that the Nth detector 30, in the same manner as detector 24, has its output connected to filter 42 which can be a circuit similar to that of filter 34. The output of filter 42 similarly is connected to the input of a pulse timing detector 44 which again can be similar to pulse timing detector 36.

The output of pulse timing detector 44 in turn is connected as a second input to phase detector 40. Detector 40 can be any of a number of known circuits and preferably is a pulse chain phasemeter which measures the phase difference for example between the leading edges of corresponding pulses of two pulse chains, such as the circuit disclosed by F. Vrataric, Jr., "Electronic Switching in Phase Measurement" *Electronics* 32:23, pp. 60–61. As well known in the art, the output of phase detector 40 typically is a signal, the amplitude of which changes in proportion to the phase difference between the signals from detector 44 and those from the output of shift register 38. The output of phase detector 40 is preferably coupled to the input of filter 46 which is typically a low pass filter to provide a desirable servo-loop stability and smoothing of the output signal from phase detector 40.

The output of filter 46 is coupled to the control input of voltage controlled oscillator 48. The latter typically can be a known square wave oscillator, the output repetition rate of which is variable in accordance with the level of the voltage input thereto from filter 46, such as the oscillator described in *Guide Book of Electronic Circuits*, John Markus, McGraw Hill, 1974, p. 1000. The output of oscillator 48 is connected to the clock input of shift register 38 so that the variable repetition rate pulse train from oscillator 48 serves as the timing signals to vary the delay time of signals passing through shift register 38.

As is shown in the drawing, pump 50 is provided for precisely controlling the speed of the flow stream through capillary 20. Pump 50 preferably is a type which will not damage the delicate cells or particles in the flow stream, and which is very precisely controllable. To that end, pump 50 is impelled by motor 52 which in turn has its speed controlled by known motor control circuit 54. The control input to motor control circuit 54 is typically coupled to the output of filter 46 so that the motor control circuit will vary the speed of motor 52 responsively to changes in the amplitude of the error or control signal from filter 46.

It is intended that the servoloop of the present invention should not be limited to the specific elements shown, namely phase detector 40, filter 46 and VCO 48. In place of these three latter elements, one can simple employ a digital phase meter which directly generates a pulse chain having a repetition rate proportional to the phase difference of two input pulses such as the circuit disclosed by C. Schroeder et al., "Tracking Orbits of Man-Made Moons," *Electronics*, 32:1, pp. 33–37. Of course in such case the output of the digital phase meter would be used directly as the clocking input to shift register 38.

In operation of the circuit as thus far described, motor 52 drives pump 50 so that a flow stream containing the particles of interest, such as blood cells, are impelled in single file through capillary 20. As each cell traverses the capillary, it first passes between source 22a and detector 24 producing an output pulse which is filtered in filter 34 and thence fed to pulse timing detector 36. The output of detector 36 typically is a pulse having a leading edge which is coincident with the center of the pulse provided by shaper 34, and this pulse is then fed to shift register 38. The pulse is successively shifted through the several stages of shift register 38 and then supplied as one input to phase detector 40 after the time delay occasioned by the period required to shift the pulse through register 38. Preferably that time delay has a period which is approximately equal to the time required for the particle which had been detected by detector 24 to arrive at a position wherein it modulates the signal from source 22e. The modulated signal, detected by Nth detector 30 is then applied through filter 42 and the center of the filtered pulse is detected by pulse timing detector 44 which provides an output pulse having a leading edge coincident with the center of the filtered pulse. The output of pulse timing detector 44 is thence applied as the second input to phase detector 42 where it is compared by the latter with the output from shift register 38 to generate an error signal which has typically some parameter, such as voltage amplitude, proportional to the phase difference between the leading edge of the pulse output from detector 44 and the leading edge of the pulse output from shift register 38. The error signal provided by phase detector 40 is then filtered by filter 46 and applied as a control signal to voltage controlled oscillator 48. The latter in turn will provide a pulse train the repetition rate of which is proportional to the amplitude of the control signal. The pulse train output of oscillator 48 of course constitutes the clocking control or timing signal which varies the speed at which a signal is shifted through shift register 38 and therefore varies the delay provided by shift register 38.

If for example, the signal from detector 30 lags the signal from detector 24, as timed by circuits 44 and 36 respectively, it is apparent that the transit time of the particle or cell through capillary 20 does not match the preset delay time provided by shift register 38. In other words, the stream speed can be considered too slow. Phase detector 40, comparing the outputs from pulse timing detector 44 and shift register 38 will then provide an output signal which changes in magnitude proportionally to the phase difference detected. This change in signal amplitude causes the output of oscillator 48 to change in repetition rate and lengthen the delay or time period required to shift the signal through register 38. Also, because the output of filter 46 is connected to motor control 54, the change in the output signal from phase detector 40 tends to make motor 52 increase its speed and increase the pump rate. Hence, as the delay in shift register increase and the flow rate of the fluid in capillary 20 increases, the servo loop provided by phase detector 40, filter 46, oscillator 48 and register 38 then tends to bring the phase difference between the two pulse inputs to detector 40 toward a zero average time error. Similarly, if the signal from detector 30 should lead the signal from detector 24 an opposite effect occurs which results in motor 52 slowing and the delay in shift register shortening, again tending to bring the two inputs to phase detector 40 into coincidence so that the average time error between the phase of corresponding signals is zero.

In the present invention also, discrimination is used at one or more of the measuring stations represented by detectors 24, 26, 28, 30 and 32 so that if the signals produced by a particular cell or particle through capillary 20 at the various detectors satisfies a set of relations, the signals from that cell can then be converted to digital form for further processing. On the other hand, if the signals from another type of cell do not meet the predetermined relation set then the analog signals provided at the detectors by that cell will simply be ignored and no burden is placed thereby upon any digital processing equipment associated with the system. For example, assume that the output of detector 24 is a signal X, that the output of detector 26 is a signal Y and the output of detector 28 is a signal Z. Also, assume that by virtue of the nature of the particular type of signal produced by sources 22a, 22b, and 22c, a cell of interest traversing capillary 20 will produce the following unique relations:

$$Z > T_1$$

$$X + KY < T_2$$

where $K$ is a constant and $T_1$ and $T_2$ are respectively certain preselected threshhold amplitudes or values.

The block diagram of the drawing shows the logic blocks which are used to implement selection cells exhibiting the particular set of relations set out above, but it will be appreciated by those skilled in the art that any arbitrary set of relations can be chosen in like manner. To this end, the output of detector 26 is connected to the input of gated filter 58 and the output of detector 28 is similarly connected to the input of gated filter 60. These gated filters are simply filters such as filter 34 with however controllable switching circuits incorporated therein so that a signal can be produced at the output of the filter only during a period of time that the switch portion of the circuit is closed. Such gated filters are well known in the art and need be described no further here. In order to synchronize the output signals from filters 34, 58 and 60 so that they can be matched against the set of relations above noted, the output of filter 34 is coupled to the input of shift register 62 and also to the input of another shift register 64. Similarly, the output of gated filter 58 is coupled to the input of shift register 66. The clocking inputs of shift registers 62, 64 and 66 are all connected to the output of voltage control oscillator 48 so that all of the shift registers are clocked by the same timing signal and therefore remain in synchronism with one another regardless of variations in the flow stream velocity in capillary 20. Shift register 66 is intended to provide a delay between signals entering its input and emerging from its output equal to the time required for a cell to traverse capillary 20 between a position wherein it modulates signals from source 22b to the position wherein it modulates signals from source 22c. In like manner, shift register 62 is intended to provide a delay which equals the time required for a cell or particle to move through capillary 20 between a position where it modulates signals from source 22a to where it modulates signals from source 22c. Such delays of course are preset for example by selecting the number of stages between the input and output of each shift register.

One output stage of shift register 64 is connected to control the gating or the timing of switching in filter 58. A later stage in shift register 64 is connected to gated filter 60 to control the timing of switching within the latter. In like manner, successive stages of shift register 64 are coupled to successive ones of the detectors such as 32 and the like. It will be apparent therefore that the several outputs from corresponding stages in shift register 64 provide the gating signals which define the time window during which each of the gated filters permits a signal from its corresponding detector to pass through the filter. Hence, the outputs from filters 34, 58 and 60 are shown respectively as occurring at terminals respectively noted as 68, 70, and 72. Similarly, gated filter 74 has its input connected to the output of detector 32 and the output of filter 34 is coupled to terminal 76. The output of filter 42 is also coupled to terminal 78.

With proper choice of delays in registers 66 and 62, it will be apparent that the outputs from these registers and from gated filter 60 can all be made to occur substantially simultaneously. Consequently, the output of shift register 62 is connected to the input of scaling amplifier 80 which is intended to multiply the output signal from shift register 62 by the value K. The output of scaling amplifier is fed into the summing junction at the input of summing amplifier 82. Similarly, the output of shift register 66 is likewise connected to the summing input of amplifier 82. Both scaling amplifiers and summing amplifiers are well known in the art and typically comprise types of operational amplifiers such as those described in pages 54–61 of *Handbook of Operational Amplifier Applications*, first edition, 1963, Burr-Brown Research Corporation. It will be recognized then that the output from summing amplifier 82 is clearly the relation $KX + Y$.

The output of summing amplifier 82 is connected to the input of threshholding amplifier 84. The output of gated filter 60 is similarly connected to the input of another threshholding amplifier 86. The outputs of the two threshholding amplifiers 84 and 86 are connected as respective inputs to AND gate 88. Threshholding amplifiers 84 and 86 respectively provide threshhold values equivalent to $T_1$ and $T_2$ in the relations above noted. The threshholding amplifiers can typically be voltage level detectors or the like such as the variable threshhold amplifier described by C. Becklein, "Photocell Threshold Circuit," EEE April, 1967, p. 139. It will be clear that no output signal will appear at output terminal 90 of gate 88 unless the precise set of relations above noted has been satisfied by a particle or cell which has passed through capillary 20 and provided the proper signals to detectors 24, 26 and 28. Hence, an output at terminal 90 can be used preferably to enable a set of analog-to-digital converters 92 the outputs of which are connected for example to a computer memory or for direct computer processing, and the inputs to which are couple to terminals 68, 70, 72, 76 and 78. If the signal does not appear at the output of gate 90, indicating that the article passing through capillary 20 is not of the desired class, then the A-to-D converters are not enabled and the irrelevant data is not transferred to the digital computer.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. In apparatus for processing a population of items flowing serially in a stream, said apparatus having a plurality of signal sources distributed in sequence along the direction of and adjacent the flow of said stream, and a plurality of detectors each positioned in a sequence with respect to corresponding ones of said sources for detecting signals from said corresponding ones of said sources as modulated by the passage of said items past said sources, the improvement comprising, in combination;

First signal delay means for transferring a signal between the input and output of said delay means in a time period variable in accordance with a timing signal, the input of said delay means being coupled to the output of the first detector of said sequence of detectors; and means for generating said timing signal proportionally to the difference in phase between each signal appearing at the output of said delay means and each corresponding modulated signal detected by the last of the detectors in said sequence.

2. Apparatus as defined in claim 1 including means for coupling said output of said first detector to said input of said delay means.

3. Apparatus as defined in claim 2 wherein said means for coupling comprises filter means and means for generating a pulse having an edge thereof in a predetermined time relation with a selected time parameter of the output signal from said first detector.

4. Aparatus as defined in claim 3 wherein said selected parameter is the time center of the output signal from said first detector.

5. Apparatus as defined in claim 1 wherein said means for generating said timing signal comprises a phase comparator connected to the output of said delay means and coupled to the output of said last detector for comparing the phase of signals received from said delay means and said last detector to produce an error signal proportional to phase difference.

6. Apparatus as defined in claim 5 wherein said delay means is a shift register, and wherein said means for generating also comprises a controlled oscillator for providing an output pulse train having a repetition rate variable in accordance with a control signal, the output of said oscillator being connected to said shift register for clocking the latter, the control input of said oscillator being coupled to the output of said phase comparator so that said error signal constitutes said control signal to said oscillator.

7. Apparatus as defined in claim 6 wherein the delay period required to shift signals through said register is preset to approximately match the transit time required for an item to traverse said flow stream between said first and said last detectors.

8. Apparatus as defined in claim 1 including means for correlating the outputs from each of said detectors in accordance with said timing signal.

9. Apparatus as defined in claim 8 wherein said means for correlating comprises a plurality of gates each coupled to the output of a corresponding one of said detectors, and means for sequentially timing the operation of each of said gates at a rate in accordance with said timing signal.

10. Apparatus as defined in claim 9 wherein said means for sequentially timing comprises a second shift register having a plurality of shift stages, said shift register being connected so as to be clocked by said timing signal, said gates being coupled to selected stages of said shift register so as to be operated respectively by signals at said stages.

11. Apparatus as defined in claim 1 including means for converting said output signals from said detectors into digital representations.

12. Apparatus as defined in claim 11 including means for discriminating a selected group for said population of items and for enabling conversion of said output signals to said ditigal representations only for the items in said selected group.

13. Apparatus as defined in claim 12 wherein said means for discriminating comprises a logic circuit coupled to the outputs of selected ones of said detectors for providing an enabling signal which enables said means for converting.

14. Apparatus as defined in claim 13 wherein said logic circuit comprises a plurality of shift registers, each coupled to the output of a corresponding one of said selected ones of said detectors and having shift periods such that the outputs of all of said plurality of registers are substantially coincident for signals from each of said selected detectors due to the transit of one of said items past said selected detectors, and gating means operative by coincident output signals from said plurality of registers.

15. Apparatus as defined in claim 1 including means for controlling the flow rate of said items in said stream in accordance with said timing signal.

* * * * *